United States Patent [19]

Uchida et al.

[11] Patent Number: 4,694,017
[45] Date of Patent: Sep. 15, 1987

[54] 2-AMIDO 3(OXINDOL-3-YL)PROPIONIC ACIDS HAVING ANTIULCER ACTIVITY

[75] Inventors: Minoru Uchida, Komatsushima; Makoto Komatsu; Kazuyuki Nakagawa, both of Tokushima, all of Japan

[73] Assignee: Otsuka Pharmaceutical Co., Ltd., Tokyo, Japan

[21] Appl. No.: 610,574

[22] Filed: May 15, 1984

[30] Foreign Application Priority Data

May 19, 1983 [JP] Japan .................................. 58-88948
Jan. 18, 1984 [JP] Japan .................................. 59-7606

[51] Int. Cl.$^4$ .................. A61K 31/405; C07D 209/34
[52] U.S. Cl. ..................................... 514/418; 548/484
[58] Field of Search ............... 548/484, 504; 514/418, 514/419

[56] References Cited

U.S. PATENT DOCUMENTS 4,000,297 12/1976 Rovati .................................. 514/419

FOREIGN PATENT DOCUMENTS 1158532 1/1968 United Kingdom ................. 548/486
1220628 1/1971 United Kingdom ................. 548/504
1237008 6/1971 United Kingdom ................. 548/484

OTHER PUBLICATIONS

Kotake, M. et al., J. Amer. Chem. Soc. (1950), v. 72, pp. 5085-5087.
Ariens, E. S., *Drug Design*, Academic Press, New York (1971) p. 10.
Burger, Alfred, *Medicinal Chemistry*, John Wiley & Sons, New York, (1971) pp. 803-804.
McOmie, J. F. W., *Protective Groups in Organic Chemistry*, Plenum Press (1973) pp. 46-51.
Ohno, et al., ... Synthesis 1,2 Hydroxytryptamine, and its Derivatives," J. Org. Chem., vol. 17, pp. 2635-2637 (1974).

Primary Examiner—Donald G. Daus
Assistant Examiner—M. Noel
Attorney, Agent, or Firm—Finnegan, Henderson, Farabow, Garrett & Dunner

[57] ABSTRACT

Novel oxindole derivative and salt thereof represented by the general formula,

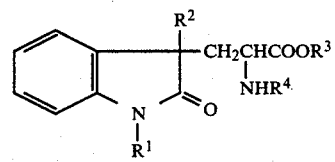

wherein $R^1$ is a hydrogen atom, a lower alkyl group, a lower alkenyl group, a lower alkynyl group or a phenyl-lower alkyl group; $R^2$ is a hydrogen atom or a lower alkyl group; $R^3$ is a hydrogen atom, a cycloalkylcarbonyl group, a benzoyl group which may have 1 to 3 substituents selected from the group consisting of a halogen atom, a lower alkyl group and a lower alkoxy group on the phenyl ring, or a phenyl-lower alkanoyl group which may have halogen atoms as the substituents on the phenyl ring; provided that when $R^4$ is a hydrogen atom, then $R^3$ should be neither a hydrogen atom nor a lower alkyl group.

The novel oxindole derivative and salt thereof possesses anti-peptic ulcer effects and are useful as anti-peptic ulcer agents.

24 Claims, No Drawings

2-AMIDO 3(OXINDOL-3-YL)PROPIONIC ACIDS HAVING ANTIULCER ACTIVITY

FIELD OF THE INVENTION

The present invention relates to novel oxindole derivative and salt thereof having anti-peptic ulcer effect, processes for preparing the same, and a pharmaceutical composition for use in an anti-peptic ulcer agent containing said oxindole derivative as the active ingredient.

The novel oxindole derivative and salt thereof according to the present invention are represented by the general formula (1),

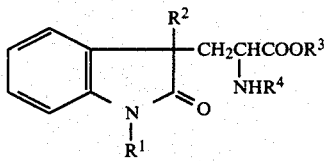

wherein $R^1$ is a hydrogen atom, a lower alkyl group, a lower alkenyl group, a lower alkynyl group or a phenyllower alkyl group; $R^2$ is a hydrogen atom or a lower alkyl group; $R^3$ is a hydrogen atom or a lower alkyl group; $R^4$ is a hydrogen atom, a cycloalkylcarbonyl group, a benzoyl group which may have 1 to 3 substituents selected from the group consisting of a halogen atom, a lower alkyl group and a lower alkoxy group on the phenyl ring, or a phenyl-lower alkanoyl group which may have halogen atoms as the substituents on the phenyl ring; provided that when $R^4$ is a hydrogen atom, then $R^3$ should be neither a hydrogen atom nor a lower alkyl group.

SUMMARY OF THE INVENTION

An object of the present invention is to provide a novel oxindole derivative and its salt represented by the general formula (1), having anti-peptic ulcer effects.

Another object of the present invention is to provide processes for preparing said oxindole derivative and its salt represented by the general formula (1).

Further object of the present invention is to provide a pharmaceutical composition for use in an anti-peptic ulcer agent containing said oxindole derivative or its salt as the active ingredient.

DETAILED DESCRIPTION OF PREFERRED EMBODIMENTS

A novel oxindole derivative and its salt of the present invention represented by the general formula (1) has anti-peptic ulcer effects and are useful as a treating agent for curing peptic ulcers in the digestive system, such as ulcers in the stomach and in the duodenum.

The oxindole derivative of the present invention particularly has prophylaxis and curing effects for treating chronic ulcers for example, experimental acetic acid-induced ulcer and cautery ulcer, with both less toxicity and side-effects, thus the oxindole derivative of the present invention is useful agent for curing chronic ulcers.

The oxindole derivative of the present invention also has effects for increasing endogenic-prostaglandin $E_2$ in mucosa of the stomach, and thus the oxindole derivative is useful as prophylaxis and curing agents for treating diseases by increasing endogenic-prostaglandin $E_2$. For example, the oxindole derivative of the present invention is useful as prophylaxis and curing agent for treating peptic ulcers by increasing endogenic-prostaglandin $E_2$ in the gastromucosa.

In the present specification, various groups in the definitions in the symbols of $R^1$, $R^2$, $R^3$ and $R^4$ are exemplified more specifically as follows.

As to the lower alkyl group, a straight- or branched-chain alkyl group having 1 to 6 carbon atoms, such as methyl, ethyl, propyl, isopropyl, butyl, isobutyl, pentyl or hexyl group can be exemplified.

As to the lower alkenyl group, a straight- or branched-chain alkenyl group having 2 to 6 carbon atoms, such as vinyl, allyl, 2-butenyl, 3-butenyl, 1-methylallyl, 2-pentenyl or 2-hexenyl group can be exemplified.

As to the lower alkynyl group, a straight- or branched-chain alkynyl group having 2 to 6 carbon atoms, such as ethynyl, 2-propynyl, 2-butynyl, 3-butynyl, 1-methyl-2-propynyl, 2-pentynyl or 2-hexynyl group can be exemplified.

As to the phenyl-lower alkyl group, a phenylalkyl group in which the alkyl moiety is a straight- or branched-chain alkyl group having 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl or 2-methyl-3-phenylpropyl group can be exemplified.

As to the cycloalkylcarbonyl group, a cycloalkylcarbonyl group having 3 to 8 carbon atoms, such as cyclopropylcarbonyl, cyclobutylcarbonyl, cyclopentylcarbonyl, cyclohexylcarbonyl, cycloheptylcarbonyl or cyclooctylcarbonyl group can be exemplified.

As to the lower alkoxy group, a straight- or branched-chain alkoxy group having 1 to 6 carbon atoms, such as methoxy, ethoxy, propoxy, isopropoxy, butoxy, tert-butoxy, pentyloxy or hexyloxy group can be exemplified.

As to the halogen atom, fluorine, chlorine, bromine or iodine atom can be exemplified.

As to the benzoyl group which may have 1 to 3 substituents selected from the group consisting of a halogen atom, a lower alkyl group and a lower alkoxy group on the phenyl ring, a benzoyl group which may have 1 to 3 substituents selected from the group consisting of a halogen atom, an alkyl group having 1 to 6 carbon atoms and an alkoxy group having 1 to 6 carbon atoms on the phenyl ring, such as benzoyl, 2-, 3- or 4-chlorobenzoyl, 2-, 3- or 4-fluorobenzoyl, 2-, 3- or 4-bromobenzoyl, 2-, 3- or 4-iodobenzoyl, 3,5-dichlorobenzoyl, 2,6-dichlorobenzoyl, 3,4-dichlorobenzoyl, 3,4-difluorobenzoyl, 3,5-dibromobenzoyl, 2-, 3- or 4-methylbenzoyl, 2-, 3- or 4-ethylbenzoyl, 4-propylbenzoyl, 3-isopropylbenzoyl, 2-butylbenzoyl, 4-hexylbenzoyl, 3-pentylbenzoyl, 4-tert-butylbenzoyl, 3,4-dimethylbenzoyl, 2,5-dimethylbenzoyl, 2-, 3- or 4-methoxybenzoyl, 2-, 3- or 4-ethoxybenzoyl, 3-propoxybenzoyl, 4-isopropoxybenzoyl, 3-butoxybenzoyl, 2-pentyloxybenzoyl, 4-tert-butoxybenzoyl, 4-hexyloxybenzoyl, 3,4-dimethoxybenzoyl, 3,4-diethoxybenzoyl, 2,5-dimethoxybenzoyl, 3-methyl-4-chlorobenzoyl, 2-chloro-6-methylbenzoyl, 2-methoxy-3-chlorobenzoyl, 3,4,5-trimethoxybenzoyl, 3,4,5-trimethylbenzoyl or 3,4,5-trichlorobenzoyl group can be exemplified.

As to the phenyl-lower alkanoyl group which may have halogen atoms as the substituents on the phenyl ring, in case that no substituent on the phenyl ring, a phenyl-lower alkanoyl group in which the alkanoyl moiety is a straight- or branched-chain alkanoyl group having 2 to 6 carbon atoms can be exemplified, while in case that the phenyl ring has the substituents, a phenylalkanoyl group having 1 to 3 halogen atoms as the substituents on the phenyl ring, such as (2-, 3- or 4-chlorophenyl)acetyl, (2-, 3- or 4-fluorophenyl)acetyl, (2-, 3- or 4-bromophenyl)acetyl, (2-, 3- or 4-iodophenyl)acetyl, (3,5-dichlorophenyl)acetyl, (2,6-dichlorophenyl)acetyl, (3,4-dichlorophenyl)acetyl, (3,4-difluorophenyl)acetyl, (3,5-dibromophenyl)acetyl, (3,4,5-trichlorophenyl)acetyl, 3-(3-chlorophenyl)propionyl, 3-(3,4-dibromophenyl)propionyl, 3-(4-iodophenyl)propionyl, 2-(2-bromophenyl)propionyl, 2-(3,5-dichlorophenyl)propionyl, 2-(4-chlorophenyl)propionyl, 4-(2-fluorophenyl)butyryl, 4-(3,4,5-trichlorophenyl)butyryl, 5-(4-chlorophenyl)valeryl, 2,2-dimethyl-3-(3-bromophenyl)propionyl, 6-(2,4-dichlorophenyl)hexanoyl, 6-(2-iodophenyl)hexanoyl, 5-(4-fluorophenyl)valeryl, 4-(2,6-dichlorophenyl)butyryl, 2-methyl-4-(4-chlorophenyl)butyryl, phenylacetyl, 3-phenylpropionyl, 2-phenylpropionyl, 4-phenylbutyryl, 5-phenylvaleryl, 2,2-dimethyl-3-phenylpropionyl, 6-phenylhexanoyl or 3-methyl-4-phenylbutyryl group can be exemplified.

The novel oxindole derivatives of the present invention also including their optical isomers.

The novel oxindole derivatives of the present invention can be prepared by various methods, for example by reaction process formula-1 as shown in the following scheme.

acid to obtain a mixed acid anhydride, then reacting said mixed acid anhydride with a compound (2) or (1b); (b) an activated ester method or activated amide method, thus a method by converting a carboxylic acid (3) into an activated ester for example p-nitrophenyl ester, N-hydroxysuccinimide ester or 1-hydroxybenzotriazole ester; or a method by converting a carboxylic acid (3) into an activated amide for example benzoxazolin-2-thione, then reacting said activated ester or activated amide with a compound of the formula (2) or (1b); (c) a carbodiimide method, thus a method by dehydrocondensing a carboxylic acid (3) with a compound of the general formula (2) or (1b) in the presence of a dehydrating agent such as dicyclohexylcarbodiimide or carbonyldiimidazole; (d) a carboxylic acid halide method, thus a method by converting a carboxylic acid (3) into a carboxylic acid halide, then reacting said halide with a compound of the general formula (2) or (1b); (e) other methods, for example, a method by converting a carboxylic acid (3) into a carboxylic acid anhydride by using for example acetic anhydride as a dehydrating agent, then reacting said carboxylic acid anhydride with a compound of the general formula (2) or (1b); or a method by reacting an ester of a carboxylic acid (3) and a lower alcohol with a compound of the general formula (2) or (1b) under a high pressure and at an elevated temperature. Further, a method in which a carboxylic acid is activated with a phosphorus compound such as Reaction process formula-1

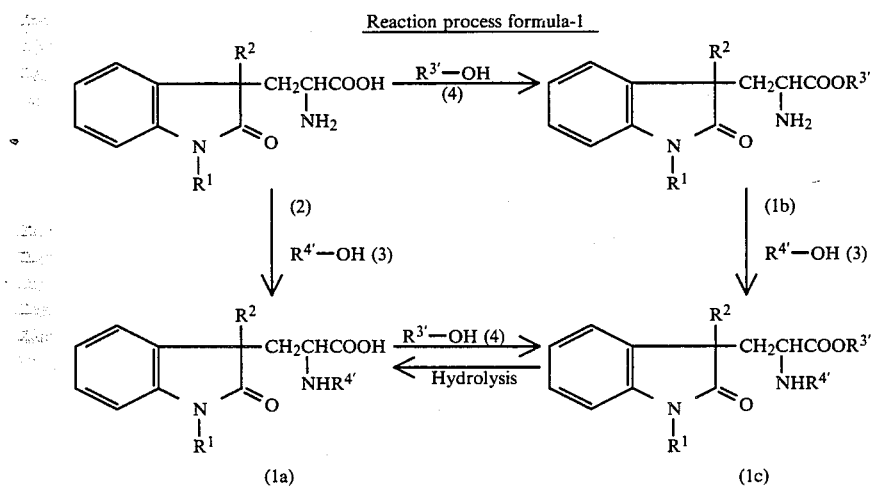

wherein $R^1$ and $R^2$ are the same as defined above; $R^{3'}$ is a lower alkyl group; $R^{4'}$ is a cycloalkylcarbonyl group, a benzoyl group which may have 1 to 3 substituents selected from the group consisting of a halogen atom, a lower alkyl group and a lower alkoxy group on the phenyl ring, or a phenyl-lower alkanoyl group which may have halogen atoms as the substituents on the phenyl ring.

Compound of the formula (2) or (1b) can be acrylated by using a carboxylic acid of the formula (3) to obtain the corresponding desired compound of the formula (1a) or (1c). Said acylation can be achieved by carrying out a common amide-bond formation reaction. In this instance, said carboxylic acid of the formula (3) may be of an activated carboxylic acid.

The amide-bond formation reaction can be carried out by applying reaction conditions used in common amidebond formation reactions. For example, (a) a mixed acid anhydride method, thus a method by reacting a carboxylic acid (3) with an alkylhalocarboxylic triphenylphosphine or diethyl chlorophosphate, then reacting said activated carboxylic acid (3) with a compound of the general formula (2) or (1b) can also be applied.

As to the alkylhalocarboxylic acid used in the mixed acid anhydride method, there can be exemplified methyl chloroformate, methyl bromoformate, ethyl chloroformate, ethyl bromoformate or isobutyl chloroformate.

The mixed acid anhydride is prepared by a method applied in a conventional Schotten-Baumann reaction, said mixed acid anhydride is reacted, without being separated from the reaction system, with a compound of the general formula (2) or (1b) to obtain a compound of the general formula (1a) or (1c) of the present invention.

The Schotten-Baumann reaction is generally carried out in the presence of a basic compound. As to the basic compound to be used is any basic compound usually used in Schotten-Baumann reaction can also be used, for example an organic base such as triethylamine, trimethylamine, pyridine, dimethylaniline, N-methylmorpholine, 4-dimethylaminopyridine, 1,5-diazabicyclo[4,3,0]nonene-5 (DBN), 1,7-diazabicyclo[5,4,0]undecene-8 (DBU) or 1,4-diazabicyclo[2,2,2]octane (DABCO); an inorganic basic compound such as potassium carbonate, sodium carbonate, potassium bicarbonate or sodium bicarbonate. Said reaction is carried out at a temperature of −20° to 100° C., preferably at 0° to 50° C., and the reaction time is about 5 minutes to 10 hours, preferably 5 minutes to 2 hours. The reaction of thus obtained mixed acid anhydride with a compound of the general formula (2) or (1b) is carried out at about −20 to 150° C., preferably at 10° to 50° C. for about 5 minutes to 10 hours, preferably about 5 minutes to 5 hours. The mixed acid anhydride method can be carried out in the absence of a solvent, but generally is carried out in a solvent. As to the solvent used in the reaction, any solvent conventionally used in a mixed acid anhydride method can also be used, specifically, a halogenated hydrocarbon such as methylene chloride, chloroform, dichloroethane; an aromatic hydrocarbon such as benzene, toluene or xylene; an ether such as diethyl ether, tetrahydrofuran or dimethoxyethane; an ester such as methyl acetate or ethyl acetate; an aprotic polar solvent such as dimethylformamide, dimethyl sulfoxide or hexamethylphosphoric triamide, can be exemplified.

In carrying out of the reaction, the ratio of the amount of a carboxylic acid (3) to the amount of an alkylhalocarboxylic acid and to the amount of a compound of the general formula (2) or (1b) is not specifically restricted, and generally at least an equimolar quantity each of these reactants are used, preferably 1 to 2 times the molar quantity of the alkylhalocarboxylic acid and of a compound of the general formula (2) or (1b) may be used to the carboxylic acid (3).

In carrying out of the above-mentioned method of (b) an activated ester method or an activated amide method, for example in using benzoxazolin-2-thionamide, the reaction can be carried out in a suitable solvent which does not give any adverse effect to the reaction, such as a solvent similar to that may be used in the above-mentioned mixed acid anhydride method or other solvent such as 1-methyl-2-pyrrolidone, at a temperature of 0° to 150° C., preferably at a temperature of 10° to 100° C., for 0.5 to 75 hours. As to a ratio of the amount of a compound of the general formula (2) or (1b) to the amount of benzoxazolin-2-thionamide is generally at least an equimolar quantity, preferably an equimolar to 2 times the molar quantity of the latter is used to the former. In using N-hydroxy-succinimide ester, a suitable basic compound for example a basic compound which can be used in the above-mentioned (d) carboxylic acid halide method can also be used to proceed the reaction advantageously.

In carrying out of the above-mentioned method of (d) a carboxylic acid halide method, a carboxylic acid (3) is reacted with a halogenating agent to prepare a carboxylic acid halide, then said carboxylic acid halide is reacted with a compound of the general formula (2) or (1b), said carboxylic acid halide may be used with or without being separated from the reaction system. The reaction of said carboxylic acid halide with a compound of the general formula (2) or (1b) can be carried out in the presence of a dehydrohalogenating agent in a solvent. As to the dehydrohalogenating agent, a common basic compound may be used, thus a basic compound other than used in Schotten-Baumann reaction can be used, for example sodium hydroxide, potassium hydroxide, sodium hydride, potassium hydride, silver carbonate, an alkali metal alcoholate such as sodium methylate or sodium ethylate can be used. An excess amount of compound of the general formula (2) or (1b) can also be used as the dehydrohalogenating agent. As to the solvent, a solvent other than used in the above-mentioned Schotten-Baumann reaction can be used, for example water, an alcohol such as methanol, ethanol, propanol, butanol, 3-methoxy-1-butanol, ethyl cellosolve or methyl cellosolve; pyridine; acetone or acetonitrile; or a mixed solvent consisting of two or more of the above-mentioned solvents can be used.

The ratio of the amount of compound of the general formula (2) or (1b) to the amount of the carboxylic acid halide is not specifically restricted, and can be selected from a wide range, generally, at least an equimolar quantity of the latter can be used to the former. The reaction temperature is generally at −30° to 180° C., preferably, about 0° to 150° C., and the reaction is generally completed for about 5 minutes to 30 hours.

The carboxylic acid halide is prepared by reacting a carboxylic acid (3) with a halogenating agent in the presence of or absence of a solvent. As to the solvent, any solvent which does not give any adverse effect to the reaction can be used, for example, an aromatic hydrocarbon such as benzene, toluene or xylene; a halogenated hydrocarbon such as chloroform, methylene chloride or carbon tetrachloride; an ether such as dioxane, tetrahydrofuran or diethyl ether; or an aprotic polar solvent such as dimethylformamide or dimethyl sulfoxide, can be used. As to the halogenating agent, a common halogenating agent which can be able to convert the hydroxyl group of the carboxylic acid can be used, for example thionyl chloride, phosphorus oxychloride, phosphorus oxybromide, phosphorus pentachloride or phosphorus pentabromide can be exemplified. The ratio of the amount of the carboxylic acid (3) to the amount of the halogenating agent is not specifically restricted and can be selected from a wide range, in case that the reaction is carried out in the absence of a solvent, the latter is used in a large excess amount to the former, while in the presence of a solvent, the latter is used in at least about an equimolar, preferably 2 to 4 times the molar quantity to the former. The reaction temperature and the reaction time are not specifically restricted, and generally the reaction is carried out at about a room temperature to 100° C., preferably 50° to 80° C., for 30 minutes to 6 hours.

Above-mentioned method in which a carboxylic acid (3) is activated with a phosphorus compound such as triphenylphosphine or diethyl chlorophosphate, then reacting said activated carboxylic acid (3) with a compound of the formula (2) or (1b), the reaction is carried out in a suitable solvent. As to the solvent, any solvent which does not give any adverse effect to the reaction can be used, and specifically, a halogenated hydrocarbon such as methylene chloride, chloroform or dichloroethane; an aromatic hydrocarbon such as benzene, toluene or xylene; an ether such as diethyl ether, tetrahydrofuran or dimethoxyethane; an ester such as methyl acetate or ethyl acetate; an aprotic polar solvent such as dimethylformamide, dimethyl sulfoxide or hexamethylphosphoric triamide can be exemplified. In this reaction, compound of the formula (2) or (1b) per se can be act as the basic compound, the reaction can be carried out preferably when the compound of the formula (2) or (1b) is used in an excess amount. If necessary, other basic compound, for example an organic basic compound such as triethylamine, trimethylamine, pyridine, dimethylaniline, N-methylmorpholine, 4-dimethylaminopyridine, 1,5-diazabicyclo[4,3,0]nonene-5 (DBN), 1,7-diazabicyclo[[5,4,0]undecene-8 (DBU) or 1,4-diazabicyclo-[2,2,2]octane (DABCO); an inorganic basic compound such as potassium carbonate, sodium carbonate, potassium bicarbonate or sodium bicarbonate can be exemplified. The reaction can be achieved at about 0° to 150° C., preferably at about 0° to 100° C., for about 1 to 30 hours. The ratio of the amount of a compound of the formula (2) or (1b) to the amount of the phosphorus compound and a carboxylic acid of the formula (3), generally, at least an equimolar quantity, preferably 1 to 3 times the molar quantity of the latter can be used to the former.

In the above-mentioned reaction process formula-1, a compound of the formula (1a) or (2) may be esterified with an alcohol (4) to obtain the corresponding objective compound of the formula (1b) or (1c).

This esterification reaction can be carried out under reaction conditions similar to those used in a conventional esterification reaction, for example (i) by dehydrocondensing in the presence of a dehydrating agent in a solvent; or (ii) by reacting in the presence of an acidic or basic catalyst in a suitable solvent. As to the solvent used in the method (i), a halogenated hydrocarbon such as methylene chloride, chloroform or dichloroethane; an aromatic hydrocarbon such as benzene, toluene or xylene; an ether such as diethyl ether, tetrahydrofuran or dimethoxyethane; an aprotic polar solvent such as dimethylformamide, dimethyl sulfoxide or hexamethylphosphoryl triamide can be exemplified.

As to the dehydrating agent, for example dicyclohexylcarbodiimide or carbonyldiimidazole can be exemplified. The ratio of the amount of a compound of the formula (1a) or (2) used to the amount of an alcohol of the formula (4) may be at least an equimolar amount, preferably an equimolar to 1.5 times the molar quantity of the latter to the former. The ratio of the amount of the dehydrating agent used to the amount of a compound of the formula (1a) or (2) is at least an equimolar quantity, preferably an equimolar to 1.5 times the molar quantity of the former to the latter. The reaction temperature is generally from a room temperature to 150° C., preferably 50° to 100° C., and the reaction is generally completed in 1 to 10 hours. As to the acidic catalyst used in the method of (ii), an inorganic acid such as hydrogen chloride gas, concentrated sulfuric acid, a phosphoric acid, a polyphosphoric acid, boron trifluoride or perchloric acid; an organic acid such as trifluoroacetic acid, trifluoromethanesulfonic acid, naphthalenesulfonic acid, p-toluenesulfonic acid, benzenesulfonic acid or ethanesulfonic acid; an acid anhydride such as .trichloromethanesulfonic acid anhydride or trifluoromethanesulfonic acid anhydride; thionyl chloride; or acetone dimethyl acetal can be exemplified. Further, an acidic ion-exchange resin can also be used as the catalyst in the present invention. As to the basic catalyst, any basic catalyst which is known in the art can be used, for example an inorganic basic compound such as sodium hydroxide, potassium hydroxide, sodium carbonate, potassium carbonate, sodium bicarbonate, potassium bicarbonate or silver carbonate; an alcoholate such as sodium methylate or sodium ethylate can be exemplified.

This reaction can be carried out in the absence or presence of a solvent. As to the solvent to be used in the reaction, any solvent which can be used in a common esterification reaction can advantageously be used, specifically, an aromatic hydrocarbon such as benzene, toleune or xylene; a halogenated hydrocarbon such as dichloromethane, dichloroethane, chloroform or carbon tetrachloride; an ether such as diethyl ether, tetrahydrofuran, dioxane or ethylene glycol monomethyl ether can be exemplified. Further, the reaction can advantageously be carried out by using a drying agent such as anhydrous calcium chloride, anhydrous copper sulfate, anhydrous calcium sulfate or phosphorus pentoxide. The ratio of the amount of a compound of the formula (1a) or (2) to the amount of an alcohol (4) in not specifically restricted and may be selected from a wide range, in case that in the absence of a solvent, an alcohol (4) is used in a great excess amount, while in the presence of a solvent, an equimolar to 5 times the molar quantity, preferably an equimolar to 2 times the molar quantity of the alcohol (4) is used to the molar quantity of the compound of the formula (1a) or (2). The reaction temperature is not specifically restricted, and generally the reaction can be carried out at from $-20°$ to 200° C., preferably at from 0° to 150° C., and the reaction is generally completed in 1 to 20 hours.

In the above-mentioned reaction process formula-1, a compound of the formula (1a) can be prepared by hydrolyzing a compound of the formula (1c). The hydrolysis of a compound of the formula (1c) can be carried out in the presence of a suitable hydrolyzing catalyst, for example a hydrohalogenic acid such as hydrochloric acid or hydrobromic acid; a mineral acid such as sulfuric acid or phosphoric acid; an inorganic alkaline compound for example, an alkali metal hydroxide such as sodium hydroxide or potassium hydroxide; an alkali metal carbonate or bicarbonate, such as sodium carbonate, potassium carbonate, sodium bicarbonate or potassium bicarbonate, in the absence or presence of a suitable solvent, for example, water or a mixed solvent of water with a lower alcohol such as methanol or ethanol, at a room temperature to 150° C., preferably at 50° to 100° C., for 0.5 to 24 hours.

Reaction process formula-2

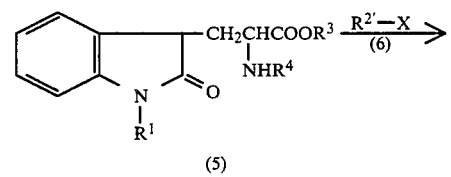

(5)

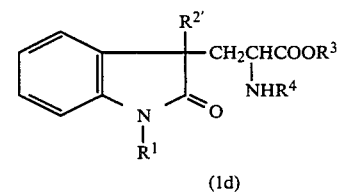

(1d)

wherein $R^1$, $R^3$ and $R^4$ are the same as defined above; $R^{2'}$ is a lower alkyl group; and X is a halogen atom.

The reaction of a compound (5) with a compound (6) is carried out in a suitable solvent, in the presence of a basic compound. As to the solvent used in this reaction is an alcohol such as methanol, ethanol or isopropanol;

an aromatic hydrocarbon such as benzene, toluene or xylene; an ether such as dioxane, diethyl ether, tetrahydrofuran or ethylene glycol dimethyl ether; a polar solvent such as dimethylformamide, dimethyl sulfoxide, hexamethylphosphoric triamide, acetone or acetonitrile; or a mixed solvent thereof. As to the basic compound used in this reaction, an inorganic basic compound such as potassium carbonate, sodium carbonate, potassium hydroxide, sodium hydroxide, sodium bicarbonate, sodium hydride or sodium amide; a tertiary amine such as triethylamine, tripropylamine, pyridine or quinoline can be exemplified.

This reaction is generally carried out at a room temperature to 150° C., preferably at a room temperature to 100° C., and the reaction is completed in 1 to about 10 hours. The ratio of the amount of a compound (10) to the amount of a compound (5) is at least equimolar quantity, preferably an equimolar to 1.5 times the molar quantity of to the latter.

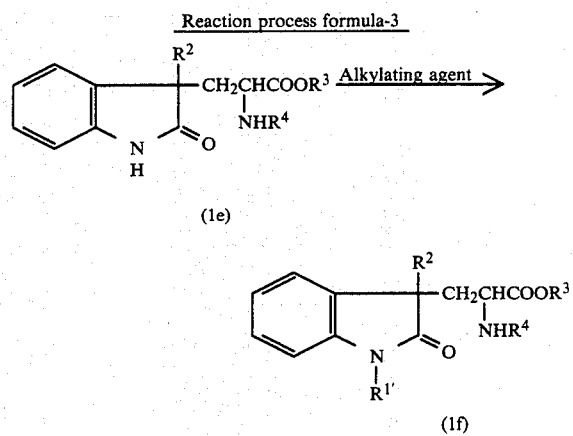

(1e)

(1f)

wherein $R^2$, $R^3$ and $R^4$ are the same as defined above; $R^{1'}$ is a lower alkyl group, a lower alkenyl group, a lower alkynyl group or a phenyl-lower alkyl group.

The alkylation of a compound of the formula (1e) is carried out in the presence of a basic compound such as sodium hydride, potassium hydride, potassium metal, sodium metal, sodium amide, potassium amide, sodium hydroxide, potassium hydroxide, sodium carbonate, potassium carbonate, sodium bicarbonate or potassium bicarbonate, in a suitable solvent.

As to the solvent used in the alkylation reaction, there are exemplified an ether such as dioxane, tetrahhydrofuran, diethyl ether or diethylene glycol dimethyl ether; an aromatic hydrocarbon such as benzene, toluene or xylene or chlorobenzene; a polar solvent such as dimethylformamide, dimethyl sulfoxide, hexamethylphosphoric triamide or ammonia water; or a mixture of these solvents.

As to the alkylating agent used in this reaction, a halogenated alkyl of the formula $R^{1'}$—X (wherein $R^{1'}$ is the same as defined above; X is a halogen atom); a dialkyl sulfate such as dimethyl sulfate or diethyl sulfate; a toluenesulfonate such as benzyl p-toluenesulfonate or methyl p-toluenesulfonate. The ratio of the amount of the alkylating agent to the amount of a compound of the formula (1e) is not specifically restricted, and generally at least an equimolar quantity, preferably an equimolar to 2 times the molar quantity of the former is used to the latter. The reaction is carried out generally at 0° to 70° C., preferably at 0° C. to a room temperature, and is generally completed in 30 minutes to 12 hours.

In the above-mentioned alkylation, according to reaction conditions used, not only 1-position but also 3-position of the oxindole skeleton may be alkylated, furhter the carboxylic acid portion in the side-chain may be alkylated. However, if a suitable reaction condition is chosen, the reaction product in which only 1-position in the oxindole skeleton is alkylated can be obtained. The partially or fully alkylated products can be isolated and purified from the reaction product by means of conventional separation methods, further the reaction products in which the carboxylic acid portion in the side-chain of 3-position can easily be converted into a compound of (1f) by treating hydrolysis reaction in a suitable hydrolyzing catalyst for example a basic compound such as sodium hydroxide, potassium hydroxide, sodium carbonate, potassium carbonate or sodium bicarbonate; or a mineral acid such as hydrochloric acid or sulfuric acid, in a suitable inert solvent for example water; a lower alcohol such as methanol or ethanol; an ether such as dioxane or tetrahydrofuran; a polar solvent such as dimethylformamide or dimethyl sulfoxide, at a room temperature to 120° C. for about 30 minutes to 6 hours.

In the above-mentioned reaction process formula-1 and -2, a compound of the general formula (5) and a compound of the general formula (2) both used as the starting materials can be prepared by method as shown in the following reaction process formula-4 and -5 respectively.

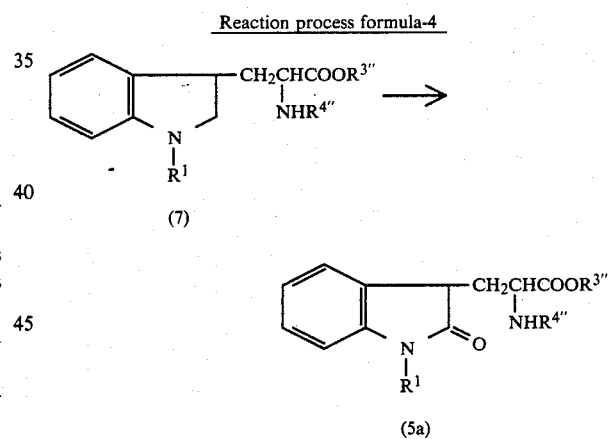

(7)

(5a)

wherein $R^1$ is the same as defined above; $R^{3''}$ is the same as defined in $R^3$; and $R^{4''}$ is the same as defined in $R^4$; provided that $R^{3''}$ and $R^{4''}$ are hydrogen atom at the same time.

There are various method for converting a known compound (7) into a compound (5a), for example, (a) a method by first halogenating a compound (7) with a halogenating agent such as chlorine, bromine, N-bromosuccinimide or N-chlorosuccinimide, then thus obtained product is catalytically hydrogenated; (b) a method by first halogenating a compound (7) with the above-mentioned halogenating agent, in the presence of a tertiary amine such as pyridine or quinoline, then thus obtained product is hydrolyzed under an acidic condition; (c) a method by reacting a compound (7) with dimethyl sulfoxide under an acidic condition. Among these methods, method (c) is the most preferable. In method (c), a compound (7) is reacted with dimethyl sulfoxide in the presence of a mineral acid such as hydrochloric acid, hydrobromic acid or sulfuric acid, at 0 to 150° C., preferably at 0° to 50° C., for 10 minutes to 24 hours. The ratio of the amounts of dimethyl sulfoxide and the mineral acid to the amount of a compound (7) is an equimolar to 10 times the molar quantity, preferably an equimolar to 7 times the molar quantity of dimethyl sulfoxide, and an equimolar to a large excess quantity, preferably a large excess quantity of the mineral acid, respectively to a compound (7).

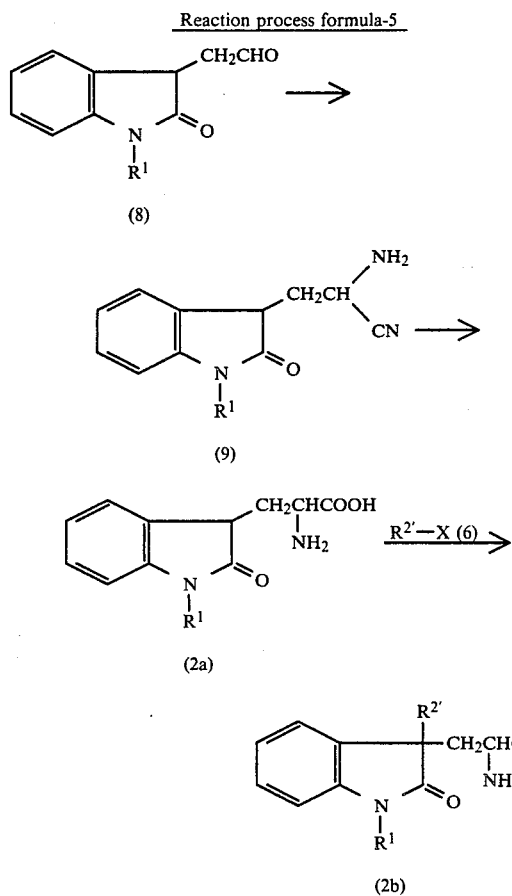

wherein $R^1$, $R^2$ and X are the same as defined above.

The reaction of changing a compound of the general formula (8) to an amino-nitrile compound of the general formula (9) is generally called as Strecker reaction, said amino-nitrile compound (9) can be obtained by reacting a compound of the general formula (8) with a cyanide such as hydrogen cyanide, potassium cyanide, sodium cyanide or cupric cyanide, in the presence of an acid and in a suitable solvent, as well as with an ammonia derivative such as ammonium chloride or ammonia.

As to the solvent used in this reaction, any solvent generally employed in Strecker reaction can be used, for example, water, an alcohol such as methanol, ethanol or isopropanol; an ether such as diethy ether, tetrahydrofuran or dioxane; or a mixed solvent of these solvents. As to the acid used in this reaction, a mineral acid such as hydrochloric acid, hydrobromic acid or sulfuric acid; an inorganic acid such as potassium bisulfite or sodium bisulfite may be exemplified. As to the ratio of the amount of cyanide compound and ammonia derivative to the amount of a compound of the general formula (8), at least an equimolar, generally an equimolar to 1.5 times the molar quantity of cyanide compound, and at least an equimolar, generally a large excess quantity of ammonia derivative may be used respectively. As to the ratio of the amount of acid to the amount of a compound of the general formula (8), at least an equimolar, preferably an equimolar to 1.5 times the molar quantity of the former may be used to the latter. The reaction may be carried out generally at 0° to 150° C., preferably at a room temperature to 100° C., for 0.5 to 10 hours.

The hydrolysis reaction of a compound of the general formula (9) may be treated in the presence of a suitable hydrolyzing catalyst for example a hydrohalogenic acid such as hydrochloric acid or hydrobromic acid; a mineral acid such as sulfuric acid or phosphoric acid; an inorganic alkali compound for example an alkali metal hydroxide such as sodium hydroxide or potassium hydroxide; carbonate or bicarbonate of alkali metal such as sodium carbonate, potassium carbonate or sodium bicarbonate, in the absence or presence of a suitable solvent for example water or a mixed solvent of water with a lower alcohol such as methanol or ethanol, at 50° to 150° C., preferably at 70° to 100° C., for about 3 to 24 hours.

The reaction of a compound of the general formula (2a) with a compound of the general furmula (6) can be carried out under conditions similar to those employed in the reaction of a compound of the general formula (5) with a compound of the general formula (6).

Compounds of the general formula (8) contain some novel compounds and can be prepared by a method as shown in the following reaction process formula-6.

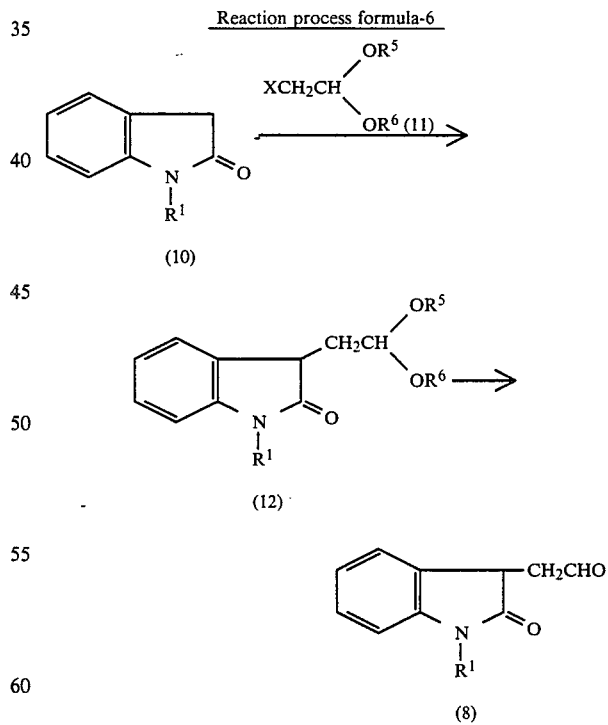

wherein $R^1$ and X are the same as defined above; $R^5$ and $R^6$ are lower alkyl group respectively.

The reaction of a compound represented by the general formula (10) with a compound represented by the general formula (11) can be carried out in a suitable solvent, in the presence of a basic compound.

As to the solvent used in this reaction, an ether such as dioxane, diethylene glycol dimethyl ether, diethyl ether or tetrahydrofuran; an aromatic hydrocarbon such as benzene, toluene, xylene or chlorobenzene; an alcohol such as methanol, ethanol or isopropanol; a polar solvent such as dimethylformamide, dimethyl sulfoxide or hexamethylphosphoric triamide; or a mixed solvent thereof can be exemplified.

As to the basic compound used in this reaction, examples are sodium hydride, potassium hydride, potassium metal, sodium metal, sodium amide, potassium amide, sodium methylate, sodium ethylate, sodium hydroxide, potassium hydroxide, sodium carbonate, potassium carbonate, sodium bicarbonate or potassium bicarbonate.

The ration of the amount of a compound of the formula (10) to the amound of a compound of the formula (11), at least an equimolar quantity, preferably an equimolar to 1.5 times the molar quantity of the former may be used to the latter. The reaction is generally conducted at 0° to 200° C., preferably at a room temperature to 150° C., and the reaction is completed in 0.5 to 15 hours. The htdrolysis of a compound of general formula (12) is carried out in a solvent for example an alcohol such as methanol or ethanol or isopropanol, or water, in the presence of a mineral acid such as hydrochloric acid or sulfuric acid, at a room temperature to the boiling point of the solvent used, for 0.5 to 30 hours.

Among the oxindole derivatives represented by the general formula (1), those having acidic group can easily form their salts with pharmaceutically acceptable bases. Such bases include inorganic bases for example metal hydroxides such as sodium hydroxide, potassium hydroxide and calcium hydroxide; alkali metal carbonates and bicarbonates such as sodium carbonate and sodium bicarbonate; alkali metal alcoholates such as sodium methylate and potassium ethylate.

Alternatively, among the oxindole derivatives represented by the general formula (1), those having basic group can easily form their salts with pharmaceutically acceptable acids. Such acids include inorganic acids for example mineral acids such as sulfuric acid, nitric acid, hydrochloric acid and hydrobromic acid; organic acids such as acetic acid, p-toluenesulfonic acid, ethanesulfonic acid, oxalic acid, maleic acid, succinic acid and benzoic acid.

Oxindole derivatives of the present invention prepared by the above-mentioned various methods can easily be isolated and purified from the reaction system by usual separation techniques such as distillation, recrystallization, column chromatography, preparative thin layer chromatogrpahy and solvent extraction.

Oxindole derivatives of the present invention are useful as anti-peptic ulcer agents, and they can be used as in the form of general preparations of pharmaceutical compositions together with usual pharmaceutically acceptable carriers. Examples of said pharmaceutically acceptable carriers which are used depending on the desired form of pharmaceutical compositions including diluents or excipients such as fillers, diluents, binders, wetting agents, disintegrators, surface-active agents and lubricants.

No particular restriction is made to the administration unit forms, and the compositions can be selected from any desired unit form including tablets, pills, powders, liquors, suspensions, emulsions, granules, capsules, suppositories and injections (solutions, suspensions and the like).

For the purpose of to shape in the form of tablets, carriers which are widely used in the field can also be used, for example excipients such as lactose, sucrose, sodium chloride, glucose, urea, starch, calcium carbonate, kaolin, crystalline cellulose, silicic acid and the like; binding agents such as water, ethanol, propanol, simple syrup, glucose solution, starch solution, gelatin solution, carboxymethyl cellulose, shelac, methyl cellulose, calcium phosphate and polyvinylpyrrolidone; disintegrators such as dried starch, sodium alginate, agar-agar powder, laminalia powder, sodium bicarbonate, calcium carbonate, esters of polyoxyethylene sorbitan fatty acids, sodium laurylsulfate, monoglyceride of stearic acid, starch and lactose; disintegration inhibitors such as sucrose, stearin, coconut butter and hydrogenated oils; absorption accelerators such as quaternary ammonium bases and sodium laurylsulfate; wetting agents such as glycerin and starch; adsorbing agents such as starch, lactose, kaolin, bentnite and colloidal silicic acid; and lubricants such as purified talc, stearic acid salts, boric acid powder and polyethylene glycols.

In case of preparing tablets, they can be further coated with usual coating materials to make them into tablets coated with sugar, tablets coated with gelatin film, tablets coated with enteric coatings, tablets coated with films or double layer tablets as well as multiple layer tablets.

For the purpose of to shape in the form of pills, any carrier which is known and used widely in this field can be used, for example, excipients such as glucose, lactose, starch, coconut butter, hydrogenated vegetable oils, kaolin and talc; binders such as powdered gum arabi, powdered trgacanth gum, geletin and ethanol; desintegrators such as laminalia and agar-agar are included.

For the purpose of to shape in the form of suppositories, carriers which are known and widely used in this field can also be used, for example, polyethylene glycols, coconut butter, higher alcohols, esters of higher alcohols, gelatin and semi-synthesized glycerides are included.

For the purpose of to make in the form of injection preparations, solutions and suspensions are sterilized and are preferably isotonic to the blood. In making injection preparations in the form of solutions, emulsions and suspensions, any carrier which is known and is widely used in this field can also be used, for example, water, ethyl alcohol, propylene glycol, ethoxylated isostearyl alcohol, polyoxylated isostearyl alcohol and polyoxyethylene sorbitan fatty acid esters are included. In these instances, adequate amounts of sodium chloride, glucose or glycerin can be added to the desired injection preparations to make them isotonic. Furthermore, usual dissolving agents, buffers, analgesic agents can be added. Further coloring materials, preservitives, perfumes, seasoning agents, sweetening agents and other medicines can also be added to the desired preparations, if necessary.

The amoung of oxindole derivative represented by the general formula (1) of the present invention to be contained in the anti-peptic ulcer composition is not specifically restricted, and it can suitably be selected from a wide range, and generally 1 to 70%, preferably 5 to 50% by weight of the oxindole derivative of the general formula (1) may be contained in the whole composition.

Oxindole derivative of the general formula (1) of the present invention, having anti-peptic ulcer effect can be used in various forms of preparations depending on the ages, the distinction of sex, the degree of symptoms and other conditions without any restriction. For example, tablets, pills, solutions, suspensions, emulsions, granules and capsules are administered orally; injection preparations are administered intraveneously singly or administered mixed with usual injection transfusions such as glucose solutions and amino acid solutions; if necessary, the injection preparations are administered singly intramuscularly, intracutaneously, subcutaneously or intraperitoneally; suppositories are administered into rectum.

The dosage of the present anti-peptic ulcer composition can be selected suitably according to the usages, the age of the patiant, the distinct of sex and other conditions as well as the degree of the symptoms, and generally said pharmaceutical compositions containing 0.6 to 50 mg/kg of body weight/day of the oxindole derivative of the general formula (1) or its salt. Further the active ingredient may be contained from 10 to 1,000 mg in the administrative unit form. The present invention will be explained more in detail by way of the following examples, in which the preparation of the compounds to be used for the starting materials will be shown as reference examples, and the preparation of the objective oxindole derivatives will be shown as Examples.

REFERENCE EXAMPLE 1

10.2 Grams of L-tryptophane was suspended in 7.8 g of dimethyl sulfoxide, then 16.6 ml of concentrated hydrochloric acid was added all at once in the suspension, and the mixture was stirred at a room temperature overnight. The crystals formed in the reaction mixture were collected by filtration, then washed with acetone and dried to obtain 9.8 g of 2-amino-3-(oxindol-3-yl)propionic acid hydrochloride. $[\alpha]_D^{20}$ +22.5° (C=1, methanol)

REFERENCE EXAMPLE 2

88.2 Grams of 1-methyl-oxindole was dissolved in 900 ml of benzene and 400 ml of dimethylformamide, then at about 15° C., 27 g of sodium hydride (60% in oil) was added gradually in the solution, the whole mixture was stirred for 1 hour. Next, a solution of 130 g of bromacetal in 100 ml of benzene was added dropwise to the reaction mixture, and the whole reaction mixture was stirred at a room temperature for 1 hour, further the reaction mixture was refluxed for 10 hours. After cooling, the reaction mixture was poured into an ice-water, the organic layer was collected by means of separatory funnel, the remaining aqueous layer was extracted with ether, and the ether extract was combined with the organic layer, then the whole organic layer was washed with water. The resultant organic layer was dried with anhydrous magnesium sulfate, and the solvent was removed by evaporation. The residue was distilled to obtain 114.4 g of 3-(2,2-diethoxyethyl)-1methyloxindole having a boiling point of 135°-185° C. 1–1.5 mmHg.

REFERENCE EXAMPLE 3

To 114 g of 3-(2,2-diethoxyethyl)-1-methyloxindole was added 110 ml of 5% hydrochloric acid aqueous solution, and the mixture was stirred at a room temperature for 3 hours. The reaction mixture was filtered and the filtrate was neutralized with sodium carbonate, then extracted with chloroform. The chloroform layer was washed with a saturated sodium chloride aqueous solution, then dried with anhydrous sodium sulfate. The solvent was removed by evaporation to obtain 89 g of 3-formylmethyl-1-methyloxindole.

REFERENCE EXAMPLE 4

89 Grams of 3-formylmethyl-1-methyloxindole and 54 g of sodium bisulfite was dissolved in a mixed solvent of 75 ml of water with 150 ml of ether, then to the resultant mixture was added dropwise a solution of 28 g of sodium cyanide with 60 ml of water, under stirring at a room temperature. The reaction mixture was stirred for 1 hour, then water was added to the reaction mixture until the crystals formed were dissolved, the whole reaction mixture was further stirred for 1 hour. The crystals formed were collected by filtration, washed with water, dried and recrystallized from benzene to obtain 30 g of 3-(2-cyano2-hydroxyethyl)-1-methyloxindole in the form of white powdery substance. Melting point: 136°-138°C.)

REFERENCE EXAMPLE 5

16 Grams of 3-(2-cyano-2-hydroxyethyl)-1methyloxindole was suspended in 20 ml of an ethanol solution of 12% ammonia, then the suspension was stirred at 60° C. for 6 hours. After cooling, 100 ml of an aqueous solution of 10% hydrochloric acid was added to the reaction mixture, and the insoluble matters were removed by filtration. The filtrate thus obtained was concentrated to dryness, to the residue obtained was added 50 ml of concentrated hydrochloric acid, then refluxed for 8 hours. The solvent was removed by evaporation, then to the resultant residue was added ethanol together with an ethanol solution of ammonia, and the precipitates were removed by filtration, then to the resultant filtrate was added ether, and the crystals formed were collected by filtration, recrystallized from isopropanol to obtain 7 g of 3-(1-methyloxindol-3-yl)-2-aminopropionic acid in the form of yellow powdery substance. Melting point: 145°-155° C. (decomp.)

REFERENCE EXAMPLE 6

10 Grams of DL-tryptophane was dissolved in a mixture of 100 ml of acetone with 20 ml of water, then to this solution was added 6 g of potassium carbonate. Under an ice-cooled condition, 9 g of 4-chlorobenzoyl chloride was added dropwise to the above-mentioned mixture, and the reaction mixture was stirred at the same temperature for 2 hours. Then, acetone was removed by evaporation, to the residue thus obtained was added water, and mixture was acidified by adding concentrated hydrochloric acid, the crystals formed were collected by filtration, and washed with water. Recrystallized from ethanol to obtain 14 g of 2-(4-chlorobenzoylamino)-3-(indol-3-yl)propionic acid. White powdery substance.

25 0 (C=1, methanol) Melting point: 237°-240° C. (decomp.) $[\alpha]_D^{25}$ 0 (C=1, methanol)

REFERENCE EXAMPLE 7

By using 10 g of D-tryptophane and 9 g of 4-chlorobenzoyl chloride, and a method similar to that described in reference Example 6, recrystallized from methanol-water, there was obtained 12.5 g of 2-(4-chlorobenzoylamino)-3-(indol-3-yl)propionic acid. Colorless needle-like crystals. Melting point: 100°-102° C. $[\alpha]_D^{20}$ +51.5° (C=1, methanol)

REFERENCE EXAMPLE 8

By using 10 g of L-tryptophane and 9 g of 4-chlorobenzoyl chloride, and a method similar to that described in reference example 6, recrystallized from methanol-water there was obtained 13.3 g of 2-(4-chlorobenzoylamino)-3-(indol-3-yl)propionic acid in the form of colorless needle-like crystals. Melting point: 100°–102° C. $[\alpha]_D^{25}$ −49.3° (C=1, methanol)

EXAMPLE 1

1.3 Grams of 2-amino-3-(oxindol-3-yl)propionic acid hydrochloride prepared in reference example 1 was dissolved in 80 ml of dimethylformamide. To this solution was added 1.2 g of triethylamine, then under an ice-cooled condition, 0.8 g of benzoyl chloride was added dropwise thereto. The reaction mixture was stirred under an ice-cooled condition for 3 hours, then the reaction mixture was concentrated under a reduced pressure, to the residue thus obtained was added water, the crystals formed were collected by filtration. Recrystallized from ethanol-water to obtain 0.5 g of 2-benzamido-3-(oxindol-3-yl)propionic acid in the form of light brown powdery substance. Melting point: 140°–142° C. (decomp.) $[\alpha]_D^{20}$ −66° (C=0.1, methanol)

Elementary analysis: For $C_{18}H_{16}N_2O_4$: Calculated (%): C, 66.66; H, 4.97; N, 8.64. Found (%): C, 65.58; H, 5.25; N, 8.63.

EXAMPLE 2

1.25 Grams of 2-amino-3-(oxindol-3-yl)propionic acid hydrochloride prepared in reference example 1, and 1.3 g of N-hydroxysuccinimide ester of p-chlorobenzoic acid were dissolved in 50 ml of dimethylformamide. To this solution was added 1.2 g of triethylamine, and the whole mixture was stirred at a room temperature for 3 hours. Dimethylformamide was removed by evaporation, then water was added to the resultant residue, the crystals formed were collected by filtration to obtain 0.68 g of 2-(4-chlorobenzoylamino)-3-(oxindol-3-yl)propionic acid 1/4-hydrate. Melting point: 133°–135° C. (decomp.) $[\alpha]_D^{25}$ −50.3° (C=1, methanol)

EXAMPLE 3

1.14 Grams of 2-amino-3-(oxindol-3-yl)propionic acid hydrochloride prepared in Reference Example 1, 1.3 g of dicyclohexylcarbodiimide (DCC) and 1.0 g of p-chlorobenzoic acid were suspended in 10 ml of dioxane, then the suspension was stirred at 60°–70° C. for 5 hours. After the reaction was completed, the solvent was removed by evaporation, to the residue thus obtained was added ether, and the crystals formed were removed by filtration. The filtrate obtained was concentrated, then the residue thus obtained was dissolved by adding chloroform, the chloroform solution was washed with water and a saturated sodium chloride aqueous solution. The chloroform solution was dried with anhydrous sodium sulfate, and the solvent was removed by evaporation. The residue was recrystallized from methanol-water to obtain 290 mg of 2-(4-chlorobenzoylamino)-3-(oxindol-3-yl)propionic acid 1/4-hydrate in the form of colorless powdery substance. Melting 25 −50.3° (C=1, methanol) point: 133°–135° C. (decomp.) $[\alpha]_D^{25}$ −50.3° (C=1, methanol)

EXAMPLE 4

1.14 Grams of 2-amino-3-(Oxindol-3-yl)propionic acid hydrochloride prepared in reference example 1, and 0.8 ml of triethylamine were suspended in 10 ml of tetrahydrofuran, then under stirring condition at a room temperature, a solution of 1.0 g of diethyl chlorophosphate with 10 ml of tetrahydrofuran was added dropwise thereto, and the reaction mixture was stirred at a room temperature for 3 hours. A solution of 1.0 g of p-chlorobenzoic acid with 10 ml of tetrahydrofuran was added dropwise to the reaction mixture, and the whole reaction mixture was stirred at a room temperature for additional 10 hours. After the reaction was completed, the crystals formed were removed by filtration, and the filtrate was concentrated, to the residue thus obtained was poured a saturated sodium bicarbonate aqueous solution, then the mixture was extracted with chloroform. The organic layer was washed with water and a saturated sodium chloride aqueous solution, then the chloroform layer was dried with anhydrous sodium sulfate, and the solvent was removed by evaporation. The thus obtained residue was recrystallized from methanol-water to obtain 0.75 g of 2-(4-chlorobenzoylamino)-3-(oxindol-3-yl)propionic acid 1/4-hydrate in the form of colorless powdery substance. Melting point: 133°–135° C. (decomp.) $[\alpha]_D^{25}$ −50.3° (C=1, methanol)

EXAMPLE 5

To a mixture of 4.84 g of p-chlorobenzoic acid and 4 ml of triethylamine with 50 ml of dimethylformamide, was added dropwise a solution of 3.87 g of isobutyl chloroformate with 2 ml of dimethylformamide, the reaction mixture was stirred at a room temperature for 30 minutes. To the reaction mixture was added dropwise a solution of 5.72 g of 2-amino-3-(oxindol-3-yl)propionic acid hydrochloride prepared in reference example 1 with 3 ml of dimethylformamide, then the whole reaction mixture was stirred at a room temperature for 30 minutes, next was stirred at 50°–60° C. for 1 hour. After the reaction was completed, the reaction mixture was poured into a large amount of a saturated sodium chloride aqueous solution, and extracted with chloroform. The chloroform layer was washed with water, and dried. The solvent was removed by evaporation to obtain crude crystals, then recrystallized from methanol-water to obtain 3.4 g of 2-(4-chlorobenzoylamino)-3-(oxindol-3-yl)propionic acid 1/4-hydrate in the form of colorless powdery substance. Melting point: 133°–135° C. (decomp.) $[\alpha]_D^{25}$ −50.3° (C=1, methanol)

EXAMPLE 6

In 100 ml of ethanol, 1.66 g of ethyl p-chlorobenzoate, 0.5 g of sodium ethylate and 1.98 g of 2-amino-3-(oxindol-3-yl)propionic acid hydrochloride prepared in Reference example 1 were added, then the mixture was placed in an autoclave, and reacted under 110 atmospheric pressure at 140°–150° C. for 6 hours. After cooling, the reaction mixture was concentrated under a reduced pressure, the residue was dissolved in 200 ml of chloroform, then the chloroform solution was washed with 1% potassium carbonate aqueous solution, diluted hydrochloric acid and water in this order, the chloroform solution was dried with anhydrous sodium sulfate. The solvent was removed by evaporation, the residue was recrystallized from methanol-water to obtain 270 mg of 2-(4-chlorobenzoylamino)-3-(oxindol-3-yl)propionic acid 1/4-hydrate in the form of colorless powdery substance. Melting point: 133–135° C. $[\alpha]_D^{25}$ −50.3° (C=1, methanol)

EXAMPLES 7–18

Similar to the above-mentioned Example 1, by using 2-amino-3-(oxindole-3-yl)propionic acid hydrochloride and other suitable starting material, there were prepared compounds as shown in Table 1 as follows.

TABLE 1

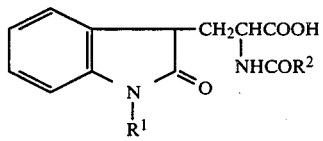

| Example No. | $R^1$ | $R^2$ | A | Crystal form | Recrystallization solvent | Melting point (°C.) | Optical rotation (C = 0.1, $[\alpha]_D^{20}$ (°) methanol) |
|---|---|---|---|---|---|---|---|
| 7 | H | cyclohexyl | — | White powdery substance | Ethyl acetate | 196–198 (decomp.) | −46 |
| 8 | H | 3-Cl-phenyl | ½-H₂O | Light yellow powdery substance | Ethanol-water | 145–147 (decomp.) | |
| 9 | H | 2,4,5-tri-OCH₃-phenyl | — | White powdery substance | Ethanol | 202–203 (decomp.) | −118 |
| 10 | H | 3,4-di-CH₃-phenyl | — | Colorless prism-like crystals | Chloroform | 237.5–239 (decomp.) | −70 |
| 11 | H | 4-Br-phenyl | ½-H₂O | Yellow powdery substance | Chloroform | 149–151 (decomp.) | −77 |
| 12 | H | 4-OCH₃-phenyl | — | Light yellow powdery substance | Chloroform | 142–146 (decomp.) | |
| 13 | H | —CH₂—(4-Cl-phenyl) | — | White powdery substance | Ethyl acetate-ethanol | 190–192 (decomp.) | −51 |
| 14 | H | 4-Cl-phenyl | ¼-H₂O | Colorless powdery substance | Methanol-water | 133–135 (decomp.) | −50.3 (C = 1.0, methanol) |
| 15 | H | —CH₂—phenyl | — | White powdery substance | Ethyl acetate-hexane | 135–140 (decomp.) | |
| 16 | H | cyclopropyl | — | White powdery substance | Ethyl acetate-ethanol | 222–224 (decomp.) | |

TABLE 1-continued

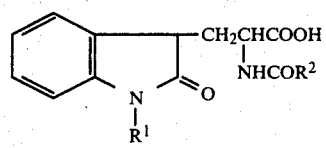

| Example No. | R¹ | R² | A | Crystal form | Recrystallization solvent | Melting point (°C.) | Optical rotation (C = 0.1, $[\alpha]_D^{20}$ (°) methanol) |
|---|---|---|---|---|---|---|---|
| 17 | H | (cyclopentyl-H) | — | White powdery substance | Ethyl acetate | 198–200 (decomp.) | |
| 18 | H | (cycloheptyl-H) | — | White powdery substance | Ethyl acetate | 177–180 (decomp.) | |

EXAMPLES 19–30

By using a method similar to that described in the above-mentioned Example 2, and a suitable starting material prepared in the reference examples, there were prepared compounds as shown in Table 2.

TABLE 2

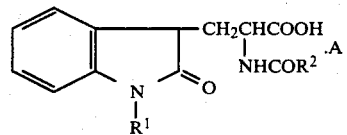

| Example No. | R¹ | R² | A | Crystal form | Recrystallization Solvent | Melting point (°C.) | Optical rotation (C = 0.1, $[\alpha]_D^{20}$ (°) methanol) |
|---|---|---|---|---|---|---|---|
| 19 | H | (cyclohexyl-H) | — | White powdery substance | Ethyl acetate | 197–198 (decomp.) | −46 |
| 20 | H | (3-Cl-phenyl) | ½-H₂O | Light yellow powdery substance | Ethanol-water | 145–147 (decomp.) | |
| 21 | H | (3,4,5-triOCH₃-phenyl) | — | White powdery substance | Ethanol | 202–203 (decomp.) | −118 |
| 22 | H | (3,5-diCH₃-phenyl) | — | Colorless prism-like crystals | Chloroform | 237.5–239 (decomp.) | −70 |
| 23 | H | (4-Br-phenyl) | ½-H₂O | Yellow powdery substance | Chloroform | 149–151 (decomp.) | −77 |

TABLE 2-continued

[Structure: indolin-2-one with N-R¹, 3-substituted with CH₂CH(NHCOR²)COOH · A]

| Example No. | R¹ | R² | A | Crystal form | Recrystallization Solvent | Melting point (°C.) | Optical rotation (C = 0.1, $[\alpha]_D^{20}$ (°) methanol) |
|---|---|---|---|---|---|---|---|
| 24 | H | -C₆H₄-OCH₃ (para) | — | Light yellow powdery substance | Chloroform | 142–146 (decomp.) | |
| 25 | H | -CH₂-C₆H₄-Cl (para) | — | White powdery substance | Ethyl acetate-ethanol | 190–192 | −51 |
| 26 | H | -C₆H₅ (phenyl) | — | Light yellow powdery substance | Methanol-water | 140–142 (decomp.) | −66 |
| 27 | H | -CH₂-C₆H₅ (benzyl) | — | White powdery substance | Ethyl acetate-hexane | 135–140 (decomp.) | |
| 28 | H | cyclopropyl | — | White powdery substance | Ethyl acetate-ethanol | 222–224 (decomp.) | |
| 29 | H | cyclopentyl | — | White powdery substance | Ethyl acetate | 198–200 | |
| 30 | H | cyclohexyl | — | White granule substance | Ethyl acetate | 177–180 | |

EXAMPLES 31–42

By using a method similar to that any one disclosed in the above-mentioned Examples 3 to 6, and a suitable starting material prepared in the reference example 1, there were prepared compounds as shown in Table 3 as follows.

TABLE 3

[Structure: indolin-2-one with N-R¹, 3-substituted with CH₂CH(NHCOR²)COOH · A]

| Example No. | R¹ | R² | A | Crystal form | Recrystallization Solvent | Melting point (°C.) | Optical rotation (C = 0.1, $[\alpha]_D^{20}$ (°) methanol) |
|---|---|---|---|---|---|---|---|
| 31 | H | cyclohexyl | — | White powdery substance | Ethyl acetate | 196–198 (decomp.) | −46 |

TABLE 3-continued

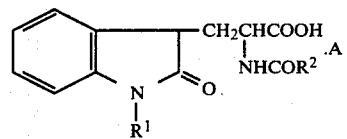

| Example No. | R¹ | R² | A | Crystal form | Recrystallization Solvent | Melting point (°C.) | Optical rotation (C = 0.1, $[\alpha]_D^{20}$ (°) methanol) |
|---|---|---|---|---|---|---|---|
| 32 | H | 4-Cl-C₆H₄- | ½-H₂O | Light yellow powdery substance | Ethanol-water | 145–147 (decomp.) | |
| 33 | H | 3,4,5-(OCH₃)₃-C₆H₂- | — | White powdery substance | Ethanol | 202–203 (decomp.) | −118 |
| 34 | H | 3,4-(CH₃)₂-C₆H₃- | — | Colorless prism-like substance | Chloroform | 237.5–239 (decomp.) | −70 |
| 35 | H | 4-Br-C₆H₄- | ½-H₂O | Yellow powdery substance | Chloroform | 149–151 (decomp.) | −77 |
| 36 | H | 4-OCH₃-C₆H₄- | — | Light yellow powdery substance | Chloroform | 142–146 (decomp.) | |
| 37 | H | -CH₂-C₆H₄-4-Cl | — | White powdery substance | Ethyl acetate-ethanol | 190–192 (decomp.) | −51 |
| 38 | H | C₆H₅- | — | Light yellow powdery substance | Methanol-water | 140–142 (decomp.) | −66 |
| 39 | H | -CH₂-C₆H₅ | — | White powdery substance | Ethyl acetate-hexane | 135–140 (decomp.) | |
| 40 | H | cyclopropyl | — | White powdery substance | Ethyl acetate-ethanol | 222–224 (decomp.) | |
| 41 | H | cyclopentyl | — | White powdery substance | Ethyl acetate | 198–200 (decomp.) | |

TABLE 3-continued

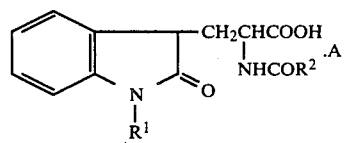

| Example No. | R¹ | R² | A | Crystal form | Recrystallization Solvent | Melting point (°C.) | Optical rotation (C = 0.1, $[\alpha]_D^{20}$ (°) methanol) |
|---|---|---|---|---|---|---|---|
| 42 | H | 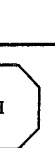 | — | White granule substance | Ethyl acetate | 177–180 (decomp.) | |

EXAMPLE 43

479 Milligrams of 2-(4-chlorobenzoylamino)-3-(oxindol-3-yl)propionic acid ¼-hydrate prepared in Example 3 and 70 mg of 50% sodium hydride (in oil) were admixed in 5 ml of dimethylformamide, and the mixture was stirred at a room temperature for 1 hour. Then a solution containing 0.23 g of methyl iodide in 3 ml of dimethylformamide was added dropwise gradually to the mixture, and the whole reaction mixture was stirred at a room temperature for 4 hours. The reaction mixture was poured into a large volume of water, and the organic material was extracted with chloroform, then the chloroform layer was washed with water and dried. Chloroform was removed by evaporation to yield 125 mg of 2-(4-chlorobenzoylamino)-3-(1-methyloxindol-3-yl)propionic acid.

Elementary analysis: For $C_{19}H_{17}N_2O_4Cl$: Calculated (%): C, 61.21: H, 4.60: N, 7.51. Found (%): C, 60.94; H, 4.83; N, 7.51.

EXAMPLE 44

479 Milligrams of 2-(4-chlorobenzoylamino)-3-(oxindol-3-yl)propionic acid ¼-hydrate prepared in Example 3 and 0.05 g of sodium amide were admixed in 5 ml of dimethylformamide, and the mixture was stirred at a room temperature for 2 hours. Then 0.17 g of allyl chloride was added to the mixture and the resulting reaction mixture was stirred at a room temperature for 10 hours. The reaction mixture was poured into 13 ml of a saturated sodium chloride aqueous solution, and the organic material was extracted with chloroform. The chloroform layer was washed with water, dried, then chloroform was removed by evaporation. The residue thus obtained was purified by means of a silica gel column chromatography to yield 85 mg of 2-(4-chlorobenzoylamino)-3-(1-allyloxyindol-3-yl)propionic acid.

Elementary analysis: For $C_{21}H_{19}N_2O_4Cl$: Calculated (%): C, 63.24; H, 4.80; N, 7.02. Found (%): C, 63.54; H, 4.51; N, 7.29.

EXAMPLE 45

479 Milligrams of 2-(4-chlorobenzoylamino)-3-(oxindol-3-yl)propionic acid ¼-hydrate prepared in Example 3 and 70 mg of 50% sodium hydride (in oil) were admixed in 5 ml of dimethylformamide, and the mixture was stirred at a room temperature for 2 hours. Then 0.17 g of propargyl chloride was added to the reaction mixture and the whole reaction mixture was stirred at a room temperature for 7 hours. The reaction mixture was poured into 13 ml of a saturated sodium chloride aqueous solution, and the organic material was extracted with chloroform. The chloroform layer was washed with water, dried, then chloroform was removed by evaporation. The residue thus obtained was purified by means of a silica gel column chromatography to yield 80 mg of 2-(4-chlorobenzoylamino)-3-[1-(2-propynyl)oxindol-3-yl]propionic acid.

Elementary analysis: For $C_{21}H_{17}N_2O_4Cl$: Calculated (%): C, 63.56, H, 4.32, N, 7.06. Found (%): C, 63.28, H, 4.57, N, 6.80.

EXAMPLE 46

479 Milligrams of 2-(4-chlorobenzoylamino)-3-(oxindol-3-yl)propionic acid ¼-hydrate prepared in Example 3 and 70 mg of 50% sodium hydride (in oil) were admixed in 5 ml of dimethylformamide, and the mixture was stirred at a room temperature for 1 hour. Then a mixture containing of 0.17 ml of benzyl chloride in 3 ml of dimethylformamide was added dropwise slowly into the reaction mixture, and the whole reaction mixture was stirred at a room temperature for 4 hours. The reaction mixture was poured into a large volume of water, and the organic material was extracted with chloroform, then the chloroform layer was dried and chloroform was removed by evaporation. There was obtained 110 mg of 2-(4-chlorobenzoylamino)-3-(1-benzyloxindol-3-yl)propionic acid.

Elementary analysis: For $C_{25}H_{21}N_2O_4Cl$: Calculated (%): C, 66.89; H, 4.72; N, 6.24. Found (%): C, 66.67; H, 4.37; N, 6.51.

EXAMPLE 47

2 Grams of 3-(1-methyloxindol-3-yl)-2-aminopropionic acid prepared in Reference Example 5 was suspended in 50 ml of 1-methyl-2-pyrrolidone, then 2.2 g of 3-(4-chlorobenzoyl)benzoxazolin-2-thione was added thereto, and the reaction mixture was stirred at a room temperature for 3 days. The reaction mixture was poured into an ice-water, and the crystals formed were collected by filtration, then the crystals were dissolved in 1N-sodium hydroxide aqueous solution, then the resulting solution was acidified by using 10%-hydrochloric acid, and the crystals formed were collected by filtration. The crystals were dried, washed with chloroform, there was obtained 1.1 g of 2-(4-chlorobenzoylamino)-3-(1-methyloxindol-3-yl)propionic acid. White powdery substance. Melting point: 115°–120° C.

Elementary analysis: For $C_{19}H_{17}N_2O_4Cl$: Calculated (%): C, 61.21; H, 4.60; N, 7.51. Found (%): C, 60.95; H, 4.81; N, 7.72.

NMR $(CDCl_3)\delta$: 2.20–2.70 (2H, m), 3.00 (3H, s), 3.60 (1H, m), 4.77 (1H, brs), 6.68 (1H, d, J=7 Hz), 6.80–7.40

(5H, m), 7.74 (2H, d, J=8 Hz), 8.78 (1H, brs), 9.62 (1H, brs);

Mass sepctrum: M+372

EXAMPLE 48

2.4 Grams of methyl 2-(4-chlorobenzoylamino)-3-(oxindol-3-yl)propionate prepared in Example 57 was dissolved in 30 ml of acetone and 10 ml of water, then 0.34 g of sodium carbonate and 1 g of methyl iodide were added thereto and the reaction mixture was refluxed for 6 hours. Acetone was removed by evaporation, and the residue was extracted with chloroform, the chloroform layer was washed with water, dried with anhydrous magnesium sulfate, then the solvent was removed by evaporation. The residue was purified by means of a silica gel column chromatography (euting agent: chloroform/methanol=100/1) then recrystallized from hexane-ethyl acetate to obtain 0.5 g of methyl 2-(4-chlorobenzoylamino)-3-(3-methyloxindol-3-yl)propionate in the form of colorless needel-like crystals. Melting point: 201°-202° C.

EXAMPLE 49

By a method similar to that described in the above-mentioned Example 48, by using a suitable starting material, there were prepared compounds as follows:

2-(4-Chlorobenzoylamino)-3-(3-methyloxindol-3-yl)propionic acid.

White powdery substance

Melting point: 190°-195° C.

NMR (CDCl$_3$)δ: 1.33 (3H, s), 2.2-2.6 (2H, m), 4.2-4.5 (1H, m), 7.10 (2H, d, J=9 Hz), 7.47 (2H, d, J=9 Hz), 6.70-8.0 (4H, m), 8.27 (1H, brs.) 9.10 (1H, brs.)

Methyl 2-(4-chlorobenzoylamino)-3-(1,3-dimethyloxindol-3-yl)propionate

Colorless flake-like crystals (recrystallized from hexane-ethyl acetate)

Melting point: 152°-153° C.

2-(4-Chlorobenzoylamino)-3-(1,3-dimethyloxindol-3-yl)propionic acid

White powdery substance

Melting point: 110°-120° C.

NMR (CDCl$_3$)δ: 1.40 (3H, s), 2.50 (2H, d, J=7 Hz), 2.80 (3H, s), 4.10-4.40 (1H, m), 7.27 (2H, d, J=9 Hz), 7.67 (2H, d, J=9 Hz), 6.70-8.10 (5H, m)

EXAMPLE 50

2.9 Grams of methyl 2-(4-chlorobenzoylamino)-3-(3-methyloxindol-3-yl)propionate prepared in Example 48 was added to 10 ml of 10%-hydrochloric acid and the mixture was refluxed for 3 hours. After cooling, the reaction mixture was extracted with chloroform, the extract was washed with water and dried with anhydrous magnesium sulfate. The solvent was removed by evaporation, the residue was dissolved in a saturated sodium bicarbonate aqueous solution, then the resulting solution was filtered with Celite (trademark for diatomaceous earth product manufactured by Johns-Manville Products Corp.) as a filter aid. The filtrate was acidified with 10%-hydrochloric acid, the crystals formed were collected by filtration to obtain 230 mg of 2-(4-chlorobenzoylamino)-3-(3-methyloxindol-3-yl)propionic acid in the form of white powdery substance.

Melting point: 190°-195° C.

NMR (CDCl$_3$) δ: 1.33 4.2-4.5 (1H, m), 7.10 (2H, d, J=9 Hz), 7.47 (2H, d, J=9 Hz), 6.70-8.0 (4H, m), 8.27 (1H, brs), 9.10 (1H, brs)

EXAMPLE 51

By a method similar to that described in Example 50, by using a suitable starting material, the following compound was prepared.

2-(4-Chlorobenzoylamino)-3-(1,3-dimethyloxindol-3-yl)propionic acid.

White powdery substance

Melting point: 110°-120° C.

NMR (CDCl$_3$)δ: 1.40 (3H, s), 2.50 (2H, d, J=7 Hz), 2.80 (3H, s), 4.10-4.40 (1H, m), 7.27 (2H, d, J=9 Hz), 7.67 (2H, d, J=9 Hz), 6.70-8.10 (5H, m)

EXAMPLE 52

6.8 Grams of 2-(4-chlorobenzoylamino)-3-(indol-3-yl)propionic acid prepared in Reference Example 6 was suspended in 8 g of dimethyl sulfoxide, then 17 g of concentrated hydrochloric acid was added to the suspension, and the resulting mixture was stirred at a room temperature for 2 hours. Further, 80 ml of water was added to the reaction mixture and stirred at a room temperature for 1 hour. The crystals formed were collected by filtration, washed with water, and dried. The crude crystals thus obtained were suspended in a mixture of chloroform:methanol=50:1 and stirred, the crystals were collected by filtration, and dissolved in a saturated sodium bicarbonate aqueous solution. The insoluble materials were removed by filtration, the filtrate obtained was neutralized with 10%-hydrochloric acid. The crystals formed were collected by filtration, washed with water, dried to obtain 3.2 g of 2-(4-chlorobenzoylamino)-3-(oxindol-3-yl)propionic acid monohydrate.

Melting point: 189°-190° C. $[\alpha]_D^{25}$ 0° (C=1, methanol)

NMR (DMSO)δ: 2.0-2.6 (m, 2H), 3.3-3.5 (m, 1H), 4.6-4.9 (m, 1H), 6.7-7.5 (m, 4H), 7.53 (2H, d, J=9 Hz), 7.93 (2H, d, J=9 Hz), 8.87-8.98 (1H, J=8 Hz), 10.43 (1H, bs), 12.0 (1H, br)

EXAMPLE 53

Using 2-(4-chlorobenzoylamino)-3-(indol-3-yl)propionic acid prepared in Reference Example 7 as the starting material, and by a method similar to that described in Example 52, there was prepared 2-(4-chlorobenzoylamino)-3-(oxindol-3-yl)propionic acid ¾-hydrate.

Melting point: 136° C. $[\alpha]_D^{25}$+92.4° (C=1, methanol)

NMR (DMSO)δ: 2.0-2.5 (m, 2H), 3.3-3.5 (m, 1H), 4.5-4.9 (m, 1H), 6.7-7.5 (m, 4H), 7.53 (2H, d, J=9 Hz), 7.90 (2H, d, J=9 Hz), 8.87, 8.98 (1H, d, J=8 Hz), 10.43 (1H, bs), 11.5 (1H, br)

EXAMPLE 54

By using 2-(4-chlorobenzoylamino)-3-(indol-3-yl)propionic acid prepared in Reference Example 8 as the starting material, and a method similar to that described in Example 52, there was prepared 2-(4-chlorobenzoylamino)(oxindol-3-yl)propionic acid ¼-hydrate. Melting point: 133°-135° C. (decomp.) $[\alpha]_D^{25}$−50.3° (C=1, methanol)

powdery substance (recrystallized from methanol-water)

EXAMPLE 55

By using a method similar to that described in Example 54, and a suitable starting material, there were prepared compounds of Examples 3, 32–42, respectively.

EXAMPLE 56

1.39 Grams of 3-(1-methyloxindol-3-yl)-2-aminopropionic acid prepared in Reference Example 5 and 1.3 g of p-chlorobenzoic acid N-hydroxysuccinimide ester were dissolved in 50 ml of dimethylformamide. Then 1.2 g of triethylamine was added thereto and the resulting mixture was stirred at a room temperature for 3 hours. Dimethylformamide was removed by evaporation, to the residue thus obtained was added with water and crystals formed were collected by filtration, there was obtained 0.75 g of 2-(4-chlorobenzoylamino)-3-(1-methyloxindol-3-yl)propionic acid.

Melting point: 115°–120° C.

Elementary analysis: For $C_{19}H_{17}N_2O_4Cl$: Calculated (%): C, 61.21; H, 4.60; N, 7.51. Found (%): C, 60.98; H, 4.79; N, 7.74.

NMR (CDCl$_3$)δ: 2.20–2.70 (2H, m), 3.00 (3H, s), 3.60 (1H, m), 4.77 (1H, brs), 6.68 (1H, d, J=7 Hz), 6.80–7.40 (5H, m), 7.74 (2H, d, J=8 Hz), 8.78 (1H, brs), 9.62 (1H, brs)

Mass spectrum: $M^{30}$ 372

EXAMPLE 57

19 Grams of 2-(4-chlorobenzoylamino)-3-(oxindol3-yl)propionic acid ¼-hydrate prepared in Example 3 was dissolved in 30 ml of methanol, then to this solution was added dropwise 9.4 g of thionyl chloride under an ice-cooled condition, then the reaction mixture was stirred at a room temperature overnight. Methanol was removed by evaporation, the residue thus obtained was extracted with chloroform, and the extract was dried with anhydrous sodium sulfate, then the solvent was removed by evaporation. The resulting residue was purified by means of a silica gel column chromatography (eluting agent: chloroform/methanol=40/1) to obtain 10.5 g of methyl 2-(4-chlorobenzoylamino)-3-(oxindol-3-yl)propionate. The chemical structure of this product was determined by means of NMR method.

NMR (CDCl$_3$)δ: 2.1–2.8 (2H, m), 3.30–3.60 (1H, m) 3.67 (1H, m), 4.60–4.85 (1H, m), 6.60–7.20 (4H, m), 7.33 (2H, d, J=8 Hz), 7.77 (2H, d, J=8 Hz), 8.90 (1H, d, J=8 Hz), 10.10 (1H, bs).

EXAMPLE 58

By using 2-(4-chlorobenzoylamino)-3-(1-methyloxinol-3-yl)propionic acid prepared in Examples 47 and 56 respectively, and a method similar to that described in Example 57, the following product was prepared.

Methyl 2-(4-chlorobenzoylamino)-3-(1-methyloxindol-3-yl)propionate

Oily substance

NMR (CDCl$_3$)δ: 2.1–2.8 (2H, m), 3.07, 3.13 (3H, s), 3.4–3.7 (1H, m), 3.63, 3.70 (3H, s), 4.70–5.00 (1H, m), 6.80 (1H, d, J=8 Hz), 7.00–7.40 (3H, m), 7.40 (2H, d, J=8 Hz), 7.83 (2H, d, J=8 Hz), 8.23, 8.53 (1H, d, J=8 Hz)

EXAMPLE 59

By using 1.33 g of methyl 2-amino-3-(1,3-dimethyloxindol-3-yl)propionate, 1.2 g of triethylamine and 0.8 g of benzoyl chloride, and a method similar to that described in Example 1, there was prepared methyl 2-(4-chlorobenzoylamino)-3-(1,3-dimethyloxindol-3-yl)propionate in the form of colorless flake-like crystals (recrystallized from hexane-ethyl acetate). Melting point: 152°–153° C.

EXAMPLE 60

By using a method similar to that described in Example 59, and a suitable starting material, there were prepared compounds as follows:

Methyl 2-(4-chlorobenzoylamino)-3-(3-methyloxindol-3-yl)propionate

Colorless needle-like crystals (recrystallized from hexane-ethyl acetate)

Melting point: 201°–202° C.

Methyl 2-(4-chlorobenzoylamino)-3-(oxindol-3-yl)propionate

White powdery substance

NMR (CDCl$_3$)δ: 2.1–2.8 (2H, m), 3.30–3.6 (1H, m), 3.67 (1H, m), 4.60–4.85 (1H, m), 6.60–7.20 (4H, m), 7.33 (2H, d, J=8 Hz), 7.77 (2H, d, J=8 Hz), 8.90 (1H, d, J=8 Hz), 10.10 (1H, bs).

2-(4-Chlorobenzoylamino)-3-(3-methyloxindol-3-yl)propionic acid

White powdery substance

Melting point: 190°–195° C.

NMR (CDCl$_3$)δ: 1.33 (3H, s), 2.2–2.6 (2H, m), 4.2–4.5 (1H, m), 7.10 (2H, d, J=9 Hz), 7.47 (2H, d, J=9 Hz), 6.70–8.0 (4H, m), 8.27 (1H, brs.), 9.10 (1H, brs.).

2-(4-Chlorobenzoylamino)-3-(1,3-dimethyloxindol-3-yl)propionic acid

White powdery substance

Melting point: 110°–120° C.

NMR: 1.40 (3H, s), 2.50 (2H, d, J=7 Hz), 2.80 (3H, s), 4.10–4.40 (1H, m), 7.27 (2H, d, J=9 Hz), 7.67 (2H, d, J=9 Hz), 6.70–8.10 (5H, m).

Methyl 2-(4-chlorobenzoylamino)-3-(1-methyloxindol-3-yl)propionate

Oily substance

NMR (CDCl$_3$)δ: 2.1–2.8 (2H, m), 3.07, 3.13 (3H, s), 3.4–3.7 (1H, m), 3.63, 3.70 (3H, s), 4.70–5.00 (1H, m), 6.80 (1H, d, J=8 Hz), 7.00–7.40 (3H, m), 7.40 (2H, d, J=8 Hz), 7.83 (2H, d, J=8 Hz), 8.23, 8.53 (1H, d, J=8 Hz).

| Example of pharmaceutical composition - 1 Preparation of film coated tablets | |
|---|---|
| 2-(4-Chlorobenzoylamino)-3-(oxindol-3-yl)propionic acid | 150 g |
| Avicel (Trademark for microcrystalline cellulose, manufactured by Asahi Chemical Industries, Ltd.) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

2-(4-Chlorobenzoylamino)-3-(oxindol-3-yl)propionic acid, Avicel, corn starch and magnesium stearate were admixed together and the mixture was ground, and compressed into tablets form by using a punch having a diameter of 10 mm. The tablets obtained were coated with a film coating composition consisting of hydroxypropylmethyl cellulose, polyethylene glycol-6000, castor oil and methanol, to prepare film coated tablets.

| Example of pharmaceutical composition - 2 Preparation of film coated tablets | |
| --- | --- |
| 2-Benzamido-3-(oxindol-3-yl)-propionic acid | 150 g |
| Citric acid | 1.0 g |
| Lactose | 33.5 g |
| Dicalcium phosphate | 70.0 g |
| Pluronic F-68 (Trademark for a nonionic series of polyoxyalkylene derivatives of propylene glycol, manufactured by BASF-Wyandotte Corp.) | 30.0 g |
| Sodium lauryl sulfate | 15.0 g |
| Polyvinylpyrrolidone | 15.0 g |
| Polyethylene glycol (Carbowax-1500) | 4.5 g |
| Polyethylene glycol (Carbowax-6000) | 45.0 g |
| Corn starch | 30.0 g |
| Dried sodium lauryl sulfate | 3.0 g |
| Dried magnesium stearate | 3.0 g |
| Ethanol | q.s. |

2Benzamido-3-(oxindol-3-yl)propionic acid, citric acid, lactose, dicalcium phosphate, Pluronic F-68 and sodium lauryl sulfate were admixed together, and the mixture thus obtained was sieved through No. 60 sieve, then the sieved mixture was wet granulated with an alcoholic solution containing polyvinylpyrrolidone, Carbowax-1500 and -6000. The granulated product was made into paste-like lump by adding ethanol, if necessary. Corn starch was added thereto and the mixture was well mixed until uniform granules were formed. The granules were sieved through No. 1 sieve, and the granules sieved were placed in a tray and dried at 100° C. in an oven for 12 to 14 hours. The dried granules were sieved through No. 16 sieve, and to this sieved granules were added dried sodium lauryl sulfate together with dried magnesium stearate, then the whole mixture was admixed well and were compressed into the shape of desired form by using a tablet machine to prepare tablets to be used for the core portions of coated tablets. The core portions were treated with a varnish, and further said treated surface of the core portions were coated with tall for preventing the surface from the absorption of moisture. Said treated surface of core portions were further coated with a primary coating layer, and further coated with a varnish to make a sufficient number of layers for preparing coated tablets for oral administration. In order to make the coated core portions of tablets into complete spherical form and to make the treated surface smoothly, the coated tablets were further coated with primary coating layers and smoothing coating layers. The coated tablets were color coated until the desired color of the surface was obtained. After the coated tablets were dried, the surface thereof were polished to make them uniform gloss.

| Example of pharmaceutical composition - 3 Preparation of injection composition | |
| --- | --- |
| 2-(4-Chlorobenzoylamino)-3-(oxindol-3-yl)propionic acid | 5.0 g |
| Polyethylene glycol (Molecular weight: 4,000) | 0.3 g |
| Sodium chloride | 0.9 g |
| Polyoxyethylene sorbitan monooleate | 0.4 g |
| Sodium metabisulfite | 0.1 g |
| Methyl para-hydroxybenzoate | 0.18 g |
| Propyl para-hydroxybenzoate | 0.02 g |
| Distilled water for injection | 100 ml |

Above-mentioned methyl para-hydroxybenzoate, propyl para-hydroxybenzoate, sodium metabisulfite and sodium chloride were dissolved in a half volume of the above-mentioned distilled water at 80° C. under stirring. The solution thus obtained was cooled to 40° C., then 2-(4-chlorobenzoylamino)-3-(oxindol-3-yl)propionic acid, polyethylene glycol and polyoxyethylene sorbitan monooleate were dissolved, in this order, in the above-mentioned solution. The remaining half volume of distilled water for injection was added to said solution to make the volume of the injection composition into the predetermined volume, then the resulting solution was sterilized by means of a sterilizing filtration using a suitable filter paper to prepare an injection preparation.

Pharmacological Test

Anti-peptic ulcer effects of the present oxindole derivatives were determined by the following pharmacological test.

| (1) Test compounds | |
| --- | --- |
| 1. | 2-(4-Chlorobenzoylamino)-3-(oxindol-3-yl)-propionic acid (Compound of Example 2) |
| 2. | 2-Benzamido-3-(oxindol-3-yl)propionic acid (Compound of Example 1) |
| 3. | 2-(Cyclohexylcarbonylamino)-3-(oxindol-3-yl) propionic acid (Compound of Example 7) |
| 4. | 2-[(4-Chlorophenyl)acetylamino]-3-(oxindol-3-yl)-propionic acid (Compound of Example 13) |
| 5. | 2-(4-Chlorobenzoylamino)-3-(1-methyloxindol-3-yl)propionic acid (Compound of Example 47) |
| 6. | 2-(4-Chlorobenzoylamino)-3-(1,3-dimethyloxindol-3-yl)propionic acid (Compound of Example 49) |
| 7. | Sucralfate (Sucrose hydrogen sulfate basic aluminium salt) |

(2) Method of the Test

Under anesthetized with ether, the venter of a rat was incised to take out the stomach. By using a microsyringe, 15 ml of 30% acetic acid was injected, from the serosa-side, to submucous membrane of the bifurcation of paries anterior ventriculi and vestibule of pylorus. The injected portion of the bifurcation was kept pressing for a few seconds to prevent the leakage of the injected fluid. The incised portion of the venter was sutured, and the rat was fasted for overnight, then a test compound was orally administered in the amount of 10 or 20 mg/kg/each administration, twice a day, i.e., in the morning and in the evening, for 9 days. Four (4) hours after of the final administration of the test compound, the rat was killed by dislocation of the collum, then the stomach was enucleated from the rat, and the stomach was fixated by injecting 10 ml of 1%-formalin solution. The fixated stomach was cut out along the great flexura line and the ulceration area (mm$^2$) of the stomach (hereinafter referred to as an ulceration index) was measured by using an orthoscopic microscope (magnification: ×10), and the curative ratio of the test compound was calculated from the following equation:

$$\text{Curative ratio (\%)} = \frac{a - b}{a} \times 100$$

wherein
a = ulceration index of the reference group
b = ulceration index of the test compound group (A rat of the reference group was administered with water or 0.5%-carboxymethyl cellulose aqueous solution.)

(3) The Test Results

The test results are shown in the following Table 4.

TABLE 4

| Test compound No. | Curative ratio (%) | Dosage (mg/kg/day) |
|---|---|---|
| 1 | 31.5 | 20 |
| 2 | 27.8 | 20 |
| 3 | 37.7 | 20 |
| 4 | 19.5 | 40 |
| 5 | 18.9 | 40 |
| 6 | 15.2 | 40 |
| 7 (Sucralfate) | 29.0 | 1,000 |

What is claimed is:

1. Oxindole compounds and pharmaceutically acceptable salts thereof represented by the formula:

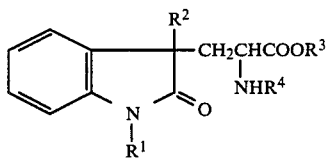

wherein $R^1$ is a hydrogen atom, a lower alkyl group, a lower alkenyl group, a lower alkynyl group or a phenyl-lower alkyl group; $R^2$ is a hydrogen atom or a lower alkyl group; $R^3$ is a hydrogen atom or a lower alkyl group; $R^4$ is a cycloalkylcarbonyl group, a benzoyl group which may have 1 to 3 substituents selected from the group consisting of a halogen atom, a lower alkyl group and a lower alkoxy group on the phenyl ring, or a phenyllower alkanoyl group which may have halogen atoms as the substituents on the phenyl ring.

2. The oxindole compound of claim 1, wherein $R^3$ is a hydrogen atom.

3. The oxindole compound of claim 1, wherein $R^3$ is a lower alkyl group.

4. The oxindole compound of claim 2 or 3, wherein $R^4$ is a phenyl-lower alkanoyl group which may have halogen atoms as the substituents on the phenyl ring.

5. The oxindole compound of claim 2 or 3, wherein $R^4$ is a cycloalkylcarbonyl group.

6. The oxindole compound of claim 5, wherein $R^2$ is a hydrogen atom.

7. The oxindole compound of claim 6, wherein $R^1$ is a hydrogen atom.

8. The oxindole compound of claim 6, wherein $R^1$ is a lower alkyl group, a lower alkenyl group, a lower alkynyl group or a phenyl-lower alkyl group.

9. The oxindole compound of claim 5, wherein $R^2$ is a lower alkyl group.

10. The oxindole compound of claim 2 or 3, wherein $R^4$ is a benzoyl group which may have 1 to 3 substituents selected from the group consisting of a halogen atom, a lower alkyl group and a lower alkoxy group on the phenyl ring.

11. The oxindole compound of claim 10, wherein $R^4$ is a benzoyl grouo having 1 to 3 halogen atoms as the substituents on the phenyl ring.

12. The oxindole compound of claim 11, wherein $R^2$ is a hydrogen atom.

13. The oxindole compound of claim 12, wherein $R^1$ is a hydrogen atom.

14. The oxindole compound of claim 12, wherein $R^1$ is a lower alkyl group, a lower alkenyl group, a lower alkynyl group or a phenyl-lower alkyl group.

15. The oxindole compound of claim 11, wherein $R^2$ is a lower alkyl group.

16. The oxindole compound of claim 1, wherein $R^1$ is a hydrogen atom; $R^2$ is a hydrogen atom; $R^3$ is a hydrogen atom or a lower alkyl group; $R^4$ is a cycloalkylcarbonyl group, or a benzoyl group which may have 1 to 3 substituents selected from the group consisting of a halogen atom, a lower alkyl group and a lower alkoxy group on the phenyl ring.

17. The oxindole compound of claim 16, wherein $R^4$ is a cycloalkylcarbonyl group.

18. The oxindole compound of claim 16, wherein $R^4$ is a benzoyl group which may have 1 to 3 substituents selected from the group consisting of a halogen atom, a lower alkyl group and lower alkoxy group on the phenyl ring.

19. The oxindole compound of claim 18, wherein $R^4$ is a benzoyl group having 1 to 3 halogen atoms as the substituents on the phenyl ring.

20. 2-(4-Chlorobenzoylamino)-3-(oxindol-3-yl)-propionic acid.

21. 2-Benzamido-3-(oxindol-3-yl)propionic acid.

22. 2-Cyclohexylcarbonylamino-3-(oxindol-3-yl)-propionic acid.

23. A pharmaceutical composition for use as an antipeptic ulcer agent, which contains an oxindole compound of claim 1 as the active ingredient.

24. The pharmaceutical composition of claim 23 containing an oxindole compound wherein $R^1$ is a hydrogen atom; $R^2$ is a hydrogen atom; $R^3$ is a hydrogen atom or a lower alkyl group; $R^4$ is to 3 substituents selected from the group consisting of a halogen atom, a lower akyl group and a lower alkoxy group on the phenyl ring.

* * * * *